United States Patent [19]

Ogawa

[11] 4,219,688
[45] Aug. 26, 1980

[54] PROCESS FOR PRODUCING VINYLNORBORNENE AND/OR TETRAHYDROINDENE

[75] Inventor: Masaya Ogawa, Suita, Japan

[73] Assignee: Japan Synthetic Rubber Co., Ltd., Tokyo, Japan

[21] Appl. No.: 939,891

[22] Filed: Sep. 6, 1978

[51] Int. Cl.$^2$ .................. C07C 13/32; C07C 13/46; C07C 13/54
[52] U.S. Cl. ..................................... 585/361; 585/366
[58] Field of Search ...................... 260/666 PY, 668 F; 585/361, 366

[56] References Cited

U.S. PATENT DOCUMENTS

| | | | |
|---|---|---|---|
| 3,407,239 | 10/1968 | Cameli et al. | 260/666 PY |
| 3,728,406 | 4/1973 | Vrinssen et al. | 260/666 PY |
| 4,079,091 | 3/1978 | Matsuno | 260/666 PY |

Primary Examiner—George Crasanakis
Attorney, Agent, or Firm—Oblon, Fisher, Spivak, McClelland & Maier

[57] ABSTRACT

In a process for producing vinylnorbornene and/or tetrahydroindene by the Diels-Alder reaction between butadiene and cyclopentadiene, the improvement that the intended product is obtained with high selectivity and high conversion can be achieved by carrying out said reaction in a solvent which has a molecular refraction $R_D$ of 30 or more and a boiling point of 150° C. or higher and which is thermally stable and inert to the reactants as well as to the reaction products.

19 Claims, 1 Drawing Figure

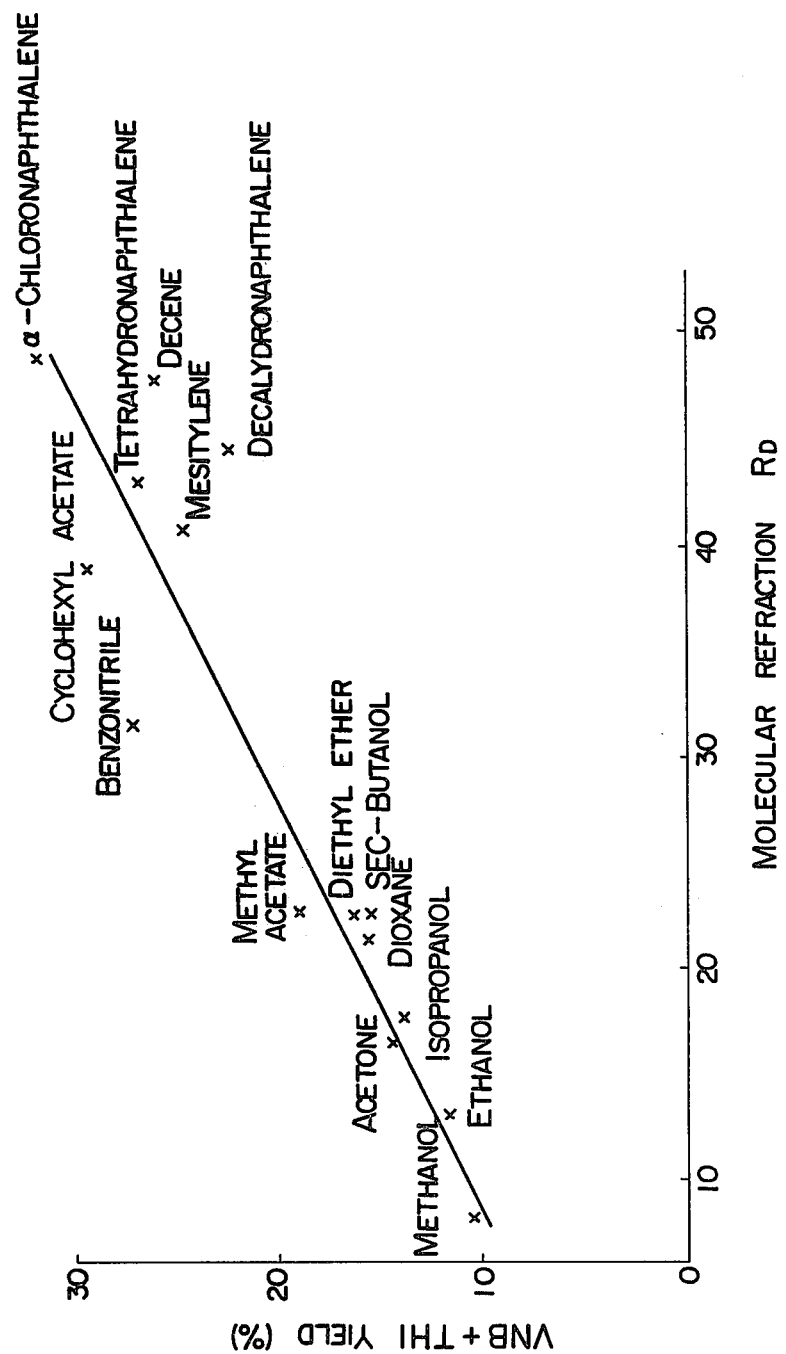

PROCESS FOR PRODUCING VINYLNORBORNENE AND/OR TETRAHYDROINDENE

BACKGROUND OF THE INVENTION

1. Field of the Invention

This invention relates to a process for producing with high selectivity 5-vinyl2-norbornene (hereinafter referred to as VNB) and/or 3a, 4,7,7a-tetrahydroindene (hereinafter referred to as THI) by the Diels-Alder reaction between butadiene and cyclopentadiene.

2. Description of the Prior Art

VNB can be isomerized to produce its isomer 5-ethylidene-2-norbornene (hereinafter referred to as ENB) which is one of the third components useful for the so-called EPT rubber.

THI can be converted to a higher polymer by the Friedel-Crafts reaction or the Diels-Alder reaction and the resultant high polymer is useful as a petroleum resin. Further, an epoxidized THI is promising as a kind of epoxy resin.

These VNB and THI can be produced by the Diels-Alder reaction between butadiene-1,3 and cyclopentadiene. However, the selectivity for VNB and/or THI is not satisfactory. In the Diels-Alder reaction between butadiene-1,3 and cyclopentadiene, there are formed, beside VNB and THI, both of which are 1:1 adducts, 4-vinylcyclohexene and 1,5-cyclooctadiene by the dimerization of butadiene-1,3, dicyclopentadiene by the dimerization of cyclopentadiene, and, further, trimers, cotrimers and even higher polymers.

Cyclopentadiene and dicyclopentadiene are in the reversible equilibrium relation that at 130° C. or more, dicyclopentadiene is apt to be converted into cyclopentadiene, while at less than 130° C., cyclopentadiene is apt to be converted into dicyclopentadiene. Further, it is known that the amount of THI formed directly from butadiene 1,3 and cyclopentadiene is less than that formed by the rearrangement of VNB which has been produced by the reaction of butadiene-1,3 and cyclopentadiene [T. Maeda, M. Muranaka, S. Hamanaka and M. Ogawa, Journal of Chemical Society of Japan, 1974 (8), 1587–9; S. Iwase, M. Nakata, S. Hamanaka, and M. Ogawa, Bulletin of Chemical Society of Japan, Vol. 49, (7) 2017–8 (1976)]. Accordingly, VNB is formed in a major amount in the earlier stage or reaction between butadiene-1,3 and cyclopentadiene or under mild reaction conditions, while the total amount of THI formed is increased in the later stage of the reaction or under severe reaction conditions because the rearrangement of VNB to THI is increased.

The use of a hydrocarbon having 5 to 7 carbon atoms or an ester of a monocarboxylic acid, said acid having 2 to 7 carbon atoms, in the Diels-Alder reaction between butadiene-1,3 and cyclopentadiene has been disclosed in Japanese Patent Publication No. 25,665/74.

The present inventors have conducted extensive research on the effect of a solvent on the reaction for producing VNB and THI from butadiene-1,3 and cyclopentadiene, and as a result, have found that the overall yield of VNB and THI is proportional to the molecular refraction $R_D$ of the solvent.

SUMMARY OF THE INVENTION

An object of this invention is to provide a process for producing with a high selectivity and a high conversion VNB and/or THI by the Diels-Alder reaction.

Other objects and advantage of this invention will become apparent from the following description.

According to this invention, there is provided a process for producing VNB and/or THI which comprises subjecting butadiene-1,3 and cyclopentadiene to the Diels-Alder reaction in a solvent which has a molecular refraction $R_D$ of 30 or more and a boiling point of 150° C. or higher and which is thermally stable and inert to the reactants as well as to the reaction products. The term "molecular refraction $R_D$" *as used in the specification and claims means a value defined by the following equation:*

$$R_D = \frac{n^2 - 1}{n^2 + 2} \cdot \frac{M}{d} = \frac{4}{3} \pi N \alpha$$

where n represents the refractive index, d represents the specific gravity, M represents the molecular weight, N represents the Avogadro number, and $\alpha$ represents the polarizability, each being determined at 20° C.

BRIEF DESCRIPTION OF THE DRAWING

FIG. 1 is a diagram representing the relationship between $R_D$ (at 20° C.) of the various solvents used in Example 2 and the Comparative Example which appear hereinafter and the overall yield (%) of VNB and THI found.

DETAILED DESCRIPTION OF THE INVENTION

Solvents having a higher molecular refraction $R_D$ are more desirable in this invention. However, it is generally about 30 or higher, preferably 35 or higher. Although there is no particular upper limit, commercially available solvents have molecular refractions of about 90 or less.

The boiling point of the solvent used in this invention is 150° C. or higher, preferably 180° C. or higher. Although no particular restriction is placed on the upper limit, the boiling point is usually 400° C. or lower, preferably 350° C. or lower. If the boiling point is below 150° C., the solvent must be removed by distillation from the reaction mixture. Since the quantity of the solvent is usually larger than that of the reaction products, the removal of the solvent by distillation results in a much larger loss of heat energy than in the case of this invention where the reaction products are taken out by distillation, allowing the solvent to remain in the vessel. This is disadvantageous from the economical viewpoint. The low-boiling solvent is also disadvantageous in that when it is used the pressure is increased during the reaction. Further, solvents having boiling points near the boiling point of VNB or THI are undesirable because it becomes difficult to separate the product from the solvent by distillation.

In the process of this invention, dicyclopentadiene may be used in place of cyclopentadiene because the former is partially decomposed under the reaction conditions into the latter which reacts with butadiene-1,3. It is not always necessary to use pure cyclopentadiene and pure dicyclopentadiene, and they may contain other paraffins or monoolefins. Some commercially available dicyclopentadiene contain impurities such as codimer of isoprene and cyclopentadiene, a codimer of piperylene and cyclopentadiene, and the like. Such a crude dicyclopentadiene may be used in the process of this invention. Similarly, a C₄ fraction containing other paraffins and monoolefins may be used in place of pure butadiene-1,3. Such crude materials containing paraffins and monoolefins may also be used as solvent, so long as they have an average $R_D$ of 30 or higher.

Examples of preferred solvents for use in the process of this invention include those hydrocarbons, particularly preferably having 10 or more carbon atoms, carboxylic esters, halohydrocarbons, nitriles and aldehydes which have a molecular refraction $R_D$ of about 30 or higher, preferably 35 or higher. They should be liquid under the reaction temperatures and pressures, inert to both the reactants and the reaction products, and non susceptible to decomposition or polymerization under the reaction conditions. They are preferably but not necessarily liquid at room temperatures.

As the hydrocarbons, there may be used any of aliphatic, aromatic and cycloaliphatic hydrocarbons, and mixtures thereof may also be used. Specifically, there are preferred cis-decahydronaphthalene ($R_D$ 43.9, boiling point 196° C.), trans-decahydronaphthalene ($R_D$ 44.3, boiling point 187° C.), n-decane ($R_D$ 48.5, boiling point 174° C.), n-decane ($R_D$ 47.7, boiling point 171° C.), tetrahydronaphthalene ($R_D$ 42.9, boiling point 208° C.), n-dodecane ($R_D$ 57.8, boiling point 216° C.), p-cymene ($R_D$ 45.3, boiling point 177° C.), n-butylbenzene ($R_D$ 45.1, boiling point 183° C.), dodecylbenzene ($R_D$ 82.2, boiling point 331° C.), mesitylene ($R_D$ 40.8, boiling point 165° C.), and those kerosenes and light oils which have $R_D$ of 30 or higher and a boiling point of 150° C. or higher, preferably 180° C. or higher.

Preferable examples of the carboxylic esters are cyclohexyl acetate ($R_D$ 39.0, boiling point 174° C.), 2-ethylhexyl acetate ($R_D$ 49.9, boiling point 197° C.), and isopentyl butyrate ($R_D$ 45.3, boiling point 185° C.).

As the halogenated hydrocarbons, there may be used any of halogenated aliphatic, aromatic or cycloaliphatic hydrocarbons. Preferable examples of the halohydrocarbons are α-chloronaphthalene ($R_D$ 48.7, boiling point 259° C.) monobromobenzene ($R_D$ 34.0, boiling point 155° C. and α-bromonaphthalene ($R_D$ 51.3, boiling point 281° C.).

Benzonitrile ($R_D$ 31.6, boiling point 191° C.) is preferred as the nitrile.

Preferable examples of the aldehydes are benzaldehyde ($R_D$ 32.0, boiling point 179° C.) and salicylaldehyde ($R_D$ 34.5, boiling point 197° C.).

These solvents may be used each alone or in admixture of two or more. Of these solvents, especially desirable are hydrocarbons, particularly decahydronaphthalene, tetrahydronaphthalene and dodecylbenzene, and those kerosenes or light oils which have a boiling point of 180° C. or higher and $R_D$ of 30 or higher, in view of thermal stability and toxicity.

Other reaction conditions are as follows:

The molar ratio of butadiene-1,3 to cyclopentadiene in the reactant mixture is preferably from 0.5 to 3.0, most preferably from 0.8 to 1.2.

The reaction temperature is preferably 120° to 250° C. The most preferable reaction temperature is 130° to 170° C. to obtain a large proportion of VNB, and 170° to 230° C. to obtain a large proportion of THI.

The weight ratio of the solvent to the total amount of butadiene-1,3 and cyclopentadiene is preferably from 0.5 to 20, most preferably 1 to 10.

The reaction pressure is that necessary for the reaction to proceed in the liquid phase.

The reaction time is preferably 15 minutes to 6 hours, most preferably 30 minutes to 2 hours to obtain VNB in a major proportion and more than 2 hours to obtain THI in a major proportion.

The reaction can be carried out either batchwise or continuously. The reactor may be either of a tank type or of a tubular type, and in either case, the reactor is preferably designed so as to be able to sufficiently remove the heat of reaction.

In the process of this invention, the reaction mixture is fractionally distilled to recover first the unreacted monomers and then the 1:1 adducts comprising VNB and THI. The almost all of the distillation residue containing dicyclopentadiene, solvent and higher polymers may be recycled to the reaction system. Alternatively, a part of the distillation residue may be first subjected to removal of the higher polymers and then recycled. Accordingly, in the process of this invention, utilities required for removing the solvent from the reaction mixture may be saved.

DESCRIPTION OF THE PREFERRED EMBODIMENTS

The invention is illustrated below in detail with reference to Examples which, however, are merely illustrative and not limitative.

In the Examples and Comparative Examples, all percentages are by weight unless otherwise indicated. The conversion, yield and selectivity in the Examples and Comparative Examples were calculated by the following equations:

$$\text{Conversion ratio} = \frac{\substack{\text{(Yield of 1:1 adduct)} + \text{(Yield} \\ \text{of trimers and higher polymers)} \\ \text{when specified solvent is used}}}{\substack{\text{(Yield of 1:1 adduct)} + \text{(Yield of} \\ \text{trimers and higher polymers)} \\ \text{when methanol is used as solvent}}}$$

$$W(g) = [\text{Total weight of reaction mixture (g)}] - [\text{weight of solvent (g)}]$$

$$\text{Conversion to dimer (\%)} = \frac{\text{Weight of dimer (g)}}{W(g)} \times 100$$

$$\text{Conversion to trimer (\%)} = \frac{\text{Weight of timer (g)}}{W(g)} \times 100$$

In a similar manner, conversion to tetramer and higher polymers (%) and unreacted monomer content (%) were calculated.

$$\text{Yield of } VNB \text{ (\%)} = [\text{Conversion to dimer (\%)}] \times [VNB \text{ content in dimer (\%)}] \times \frac{1}{100}$$

$$\text{Selectivity for } VNB \text{ (\%)} = \frac{\text{Yield of } VNB}{[100 - \text{(Unreacted monomer content)}]} \times 100$$

Selectivity for VNB (exclusive of DCPD) (%) =

$$\frac{\text{Yield of } VNB \times 100}{100 - \text{(Unreacted monomer content)} - \text{(Conversion to dimer)} \times [DCPD \text{ content in dimer (\%)}] \times \frac{1}{100}}$$

Note:
DCPD means dicyclopentadiene in the Examples and Comparative Examples.

Yield of and selectivity for (VNB+THI) were calculated in a similar manner.

EXAMPLE 1

In a stainless steel autoclave provided with an electromagnetic stirrer, an equimolar mixture of butadiene 1,3 (8.2 g) and cyclopentadiene (10 g) was mixed with an equal weight (18.2 g) of a solvent as shown in Table 1. The resulting mixture was allowed to react at 160° C. for 4 hours. The reaction mixture was allowed to stand at room temperature, and then distilled under atmospheric pressure to remove the unreacted monomers and the low-boiling solvent (which was used in Comparative Example), and thereafter subjected to distillation under reduced pressure to obtain the following fractions:

First fraction at 45°–100° C./60 mmHg
Second fraction at 80°–120° C./4 mmHg
Third fraction (residue) at above 120° C/4 mmHg The first fraction contained chiefly dimers, the second fraction contained a high-boiling point solvent and trimers, and the third fraction contained tetramers and higher polymers.

The dimer fraction was analyzed by gaschromatography. The relationship between the yield of dimer (1:1 adduct) and the $R_D$ of the solvent are shown in Table 1.

It is seen that as compared with a solvent having a small $R_D$, such as methanol or acetonitrile, the solvent specified in this invention, including decahydronaphthalene and α-chloronaphthalene, gives greater amounts of VNB and THI.

Table 1

Reaction conditions: 160° C., 4 hours.

| | Solvent | $R_D$ (20° C.) | Composition of 1:1 adduct (%) | | | | | Yield (%) | | | Conversion ratio (conversion in the case of methanol = 1.0) |
|---|---|---|---|---|---|---|---|---|---|---|---|
| | | | VCH | COD | DCPD | VNB | THI | 1:1 Adduct | Trimers and higher polymers | BD + CPD | |
| Comparative Example | Methanol | 8.2 | 0.0 | 0.0 | 93.4 | 1.3 | 5.3 | 3.1 | 1.0 | 93.1 | 1.0 |
| | Acetonitrile | 11.1 | 0.0 | 0.0 | 89.5 | 2.7 | 7.8 | 4.3 | 1.6 | 91.0 | 1.4 |
| Example | cis-Decahydronaphthalene | 43.9 | 3.2 | 0.0 | 30.1 | 48.5 | 18.2 | 50.3 | 12.8 | 33.9 | 15.4 |
| | α-Chloronaphthalene | 48.7 | 3.7 | 0.0 | 28.6 | 43.2 | 24.5 | 49.3 | 11.5 | 34.3 | 14.8 |

Note:
VCH: 4-Vinylcyclohexene
BD: Butadiene-1,3
COD: 1,5-Cyclooctadiene
CPD: Cyclopentadiene

EXAMPLE 2

In a manner similar to that in Examples 1, 8.2 g of butadiene-1,3 and 10.0 g of cyclopentadiene were placed in an autoclave. After addition of 18.2 g of a solvent (mesitylene, tetrahydronaphthalene, decahydronaphthalene, n-decene, α-chloronaphthalene, benzonitrile, salicylaldehyde or cyclohexyl acetate) or without addition of any solvent, the reactant mixture was allowed to react at 170° C. for 3 hours. The maximum pressure in the reaction system was 15–19 kg/cm².

In a manner similar to that in Example 1, the yield of the reaction product and the composition of the dimer fraction were determined. The relationships between the $R_D$ of the solvent and the yield of, selectivity for and selectivity (exclusive of DCPD) for VNB, and the yield of (VNB+THI) are shown in Table 2. The experiment without using solvent was run as Comparative Example.

Table 2

| | Solvent | | No solvent (comparative Ex.) | Mesitylene | Tetrahydronaphthalene |
|---|---|---|---|---|---|
| Reaction product | Monomer + solvent | g | 5.0 | 24.3 | 24.4 |
| | Dimer | g | 6.4 | 10.3 | 10.6 |
| | Trimer | g | 3.5 | 1.1 | 0.9 |
| | Tetramer and higher polymers | g | 3.2 | 0.7 | 0.5 |
| Conversion to | Unreacted monomer | % | 27.2 | 33.4 | 34.3 |
| | Dimer | % | 35.2 | 56.8 | 58.1 |
| | Trimer | % | 19.2 | 6.3 | 5.0 |
| | Tetramer and higher polymers | % | 17.6 | 3.8 | 2.5 |
| Composition of dimer | VCH | % | 12.1 | 2.5 | 3.1 |
| | VNB | % | 39.8 | 22.0 | 28.0 |
| | COD | % | 0.0 | 0.1 | 0.1 |
| | THI | % | 9.9 | 21.3 | 17.5 |
| | Unknown | % | 0.0 | 0.0 | 0.0 |
| | DCPD | % | 38.2 | 50.1 | 51.3 |
| VNB | Yield | % | 14.0 | 12.5 | 16.3 |
| | Selectivity | % | 19.2 | 18.8 | 24.8 |
| | Selectivity (exclusive of DCPD) | % | 23.6 | 32.8 | 45.3 |

Table 2-continued

| | | | | | |
|---|---|---|---|---|---|
| | Yield | % | 17.5 | 24.6 | 26.4 |
| VNB + THI | Selectivity | % | 24.0 | 36.9 | 40.2 |
| | Selectivity (exclusive of DCPD) | % | 29.5 | 64.5 | 73.6 |
| | $R_D$ (20° C.) | | | 40.8 | 42.9 |

| Decahydro-naphthalene | n-Decene | α-Chloro-naphthalene | Benzo-nitrile | Salicyl-aldehyde | Cyclohexyl acetate |
|---|---|---|---|---|---|
| 24.1 | 24.0 | 23.4 | 23.4 | 22.9 | 22.9 |
| 10.4 | 10.6 | 10.9 | 10.9 | 11.2 | 11.7 |
| 1.3 | 1.4 | 1.1 | 1.5 | 1.5 | 1.0 |
| 0.6 | 0.4 | 1.0 | 0.6 | 0.8 | 0.8 |
| 32.4 | 31.8 | 28.7 | 28.5 | 25.9 | 25.8 |
| 57.3 | 58.2 | 60.1 | 60.0 | 61.5 | 64.3 |
| 7.2 | 7.8 | 5.8 | 8.2 | 8.2 | 5.5 |
| 3.1 | 2.2 | 5.4 | 3.3 | 4.4 | 4.4 |
| 8.7 | 6.3 | 4.8 | 7.9 | 6.9 | 2.9 |
| 19.5 | 31.4 | 30.3 | 36.4 | 43.1 | 38.2 |
| 0.1 | 0.1 | 0.1 | 0.0 | 0.0 | 0.0 |
| 19.2 | 13.3 | 22.5 | 8.7 | 15.4 | 7.4 |
| 0.0 | 0.0 | 0.0 | 0.9 | 1.0 | 0.0 |
| 52.5 | 48.9 | 42.6 | 46.1 | 33.6 | 45.5 |
| 11.2 | 18.3 | 18.2 | 21.8 | 26.5 | 24.6 |
| 16.5 | 26.8 | 25.5 | 30.6 | 35.8 | 33.2 |
| 35.5 | 46.0 | 33.5 | 49.8 | 49.6 | 54.7 |
| 22.2 | 26.0 | 31.7 | 27.1 | 36.0 | 29.3 |
| 32.8 | 38.1 | 44.5 | 37.8 | 48.5 | 39.5 |
| 59.1 | 65.4 | 69.4 | 61.7 | 67.3 | 65.2 |
| 44.1* | 48.0 | 48.7 | 31.6 | 34.5 | 39.0 |

*cis/trans = 50/50

EXAMPLE 3

Experiments were run to examine the dependence of the yield of and selectivity for VNB on the reaction conditions. In a manner similar to that in Example 2, 8.2 g of butadiene-1,3, 10.0 g of cyclopentadiene and 18.2 g of α-chloronaphthalene as solvent were placed in an autoclave and allowed to react at 170° C. for 3 hours, or at 180° C. for 40 minutes. In Table 3, there are shown the yield of and selectivity for VNB under different reaction conditions.

Comparative Example

The procedure of Example 2 was repeated, except that methanol, ethanol, isopropanol, sec-butanol, acetone, diethyl ether, dioxane, or methyl acetate was used as a solvent. The reaction mixture was analyzed to determine the yield of VNB+THI. The results are plotted against the value of $R_D$ (20° C.) on abscissa in FIG. 1, wherein the results of Example 2 are also shown.

Table 3

| Solvent | | α-Chloronaphthalene [$R_D$ 48.7 (20° C.)] | |
|---|---|---|---|
| RD | g | 8.2 | 8.2 |
| CPD | g | 10.0 | 10.0 |
| BD/CPD | Molar ratio | 1.0 | 1.0 |
| Amount of solvent | g | 18.2 | 18.2 |
| Reaction condition | | | |
| Reaction temperature | °C. | 170 | 180 |
| Reaction time | | 3 hours | 40 min. |
| Reaction product | | | |
| Monomer + solvent | g | 23.4 | 24.4 |
| Dimer | g | 10.9 | 11.0 |
| Trimer | g | 1.1 | 0.6 |
| Tetramer and higher polymers | g | 1.0 | 0.4 |
| Conversion to | | | |
| Unreacted monomer | % | 28.7 | 33.9 |
| Dimer | % | 60.1 | 60.8 |
| Trimer | % | 5.8 | 3.3 |
| Tetramer and | | | |

Table 3-continued

| Solvent | | α-Chloronaphthalene [$R_D$ 48.7 (20° C.)] | |
|---|---|---|---|
| higher polymers | % | 5.4 | 2.0 |
| Composition of dimer | | | |
| VCH | % | 4.5 | 2.6 |
| VNB | % | 30.3 | 38.3 |
| COD | % | 0.1 | 0.0 |
| THI | % | 22.5 | 4.5 |
| Unknown | % | 0.0 | 0.0 |
| DCPD | % | 42.6 | 54.6 |
| VNB | | | |
| Yield | % | 18.2 | 23.2 |
| Selectivity | % | 25.5 | 35.2 |
| Selectivity (exclusive of DCPD) | % | 33.5 | 70.5 |
| VNB + THI | | | |
| Yield | % | 31.7 | 26.0 |
| Selectivity (exclusive | % | 44.5 | 39.4 |
| (exclusive of DCPD) | % | 69.4 | 79.1 |

Note:
BD: Butadiene-1,3

EXAMPLE 4

Four 10-liter autoclaves provided with electromagnetic stirrers were connected in series and continuously fed by means of a pump with a by-product C4-fraction (containing 45% by weight of butadiene-1,3) of the composition shown in Table 4 (410 g/hr as butadiene-1,3), obtained in the ethylene production by naphtha cracking, a crude dicyclopentadiene fraction of the composition shown in Table 5 (500 g/hr as dicyclopentadiene) and 3,640 g/hr of tetrahydronaphthalene as solvent, all of the feeds having been heated to 160° C. The reaction pressure at the exit of autoclave was maintained at 30 kg/cm² and the reaction mixture was continuously withdrawn from the autoclave and cooled. The analytical results obtained after 24 hours of the continuous reaction are shown in Tables 6 and 7.

In another run, the tetrahydronaphthalene recovered from the reaction mixture after removal of the unreacted monomers and the dimer was reused as solvent without appreciable effects on the progress of reaction.

Table 4
Composition of C₄ fraction.

| | % by weight |
|---|---|
| $C_3$ and lighter | 0.5 |
| n-Butane | 2.5 |
| Isobutane | 1.5 |
| Isobutylene | 26.4 |
| n-Butene-1 | 15.8 |
| trans-Butene-2 | 6.0 |
| cis-Butene-2 | 2.1 |
| Butadiene-1,3 | 45.0 |
| $C_5$ plus | 0.2 |

Table 5
Composition of crude DCPD

| | % by weight |
|---|---|
| DCPD | 85.0 |
| IP-CPD | 11.0 |
| PIP-CPD | 2.8 |
| $C_5$ olefin | 0.6 |
| Trimer plus | 0.6 |

Note:
IP-CPD: Codimer of isoprene and cyclopentadiene.
PIP-CPD: Codimer of piperylene and cyclopentadiene.

Table 6
Material balance of reaction

| Stream | $C_4$ feed g/hr | DCPD feed g/hr | Solvent g/hr | Reaction effluent g/hr | % |
|---|---|---|---|---|---|
| BD | 410 | | | 127 | 14.0 |
| Other $C_4$ | 501 | | | 501 | |
| DCPD + CPD | | 500 | | 194 | 21.5 |
| Other $C_{10}$ | | 88 | | 88 | |
| Tetrahydronaphthalene | | | 3,640 | 3,640 | |
| Dimer | | | | 525 | 58.0 |
| Trimer | | | | 45 | 5.0 |
| Tetramer and higher polymers | | | | 13 | 1.4 |
| Total | 911 | 588 | 3,640 | 5,133 | |

Table 7
Composition of dimer and yields of VNB and THI

Composition of dimer:

| | % by weight | g/hr |
|---|---|---|
| VCH | 2.5 | |
| VNB | 41.6 | 218.4 |
| COD | 0.1 | |
| THI | 7.8 | 41.0 |
| Unknown | 0.0 | |
| DCPD | 48.0 | 252.0 |

VNB:

| | % by weight |
|---|---|
| Yield | 24.2 |
| Selectivity | 37.5 |
| Selectivity (exclusive of DCPD) | 66.0 |

VNB + THI:

| | % by weight |
|---|---|
| Yield | 28.7 |
| Selectivity | 44.5 |
| Selectivity (exclusive of DCPD) | 78.4 |

What is claimed is:

1. In a process for producing vinylnorbornene and/or tetrahydroindene by the Diels-Alder reaction between butadiene-1,3 and cyclopentadiene, the improvement which comprises carrying out said reaction in a solvent which has a molecular refraction $R_D$ of 30 or more and a boiling point of 150° C. or higher and which is thermally stable and inert to the reactants as well as to the reaction products.

2. A process according to claim 1, wherein the solvent has a molecular refraction $R_D$ of 35 to 90.

3. A process according to claim 1 or 2, wherein the solvent is one member selected from the group consisting of hydrocarbons, halohydrocarbons, carboxylic esters, nitriles and aldehydes.

4. A process according to claim 1 or 2, wherein the solvent is a hydrocarbon having 10 or more carbon atoms.

5. A process according to claim 4, wherein the solvent is at least one compound selected from the group consisting of n-decane, n-decane, n-dodecane, tetrahydronaphthalene, decahydronaphtalene, p-cymene, n-butylbenzene, dodecylbenzene, mesitylene and those kerosenes and light oils which have a boiling point of 180° C. or higher and a molecular refraction $R_D$ of 30 or more.

6. A process according to claim 4, wherein the hydrocarbon is tetrahydronaphthalene or decahydronaphthalene.

7. A process according to claim 1, wherein the solvent is a halohydrocarbon.

8. A process according to claim 7, wherein the halohydrocarbon is an aliphatic, aromatic or cycloaliphatic halohydrocarbon.

9. A process according to claim 7, wherein the halohydrocarbon is α-chloronaphthalene, monobromobenzene or α-bromonaphthalene.

10. A process according to claim 7, wherein the halohydrocarbon is α-chloronaphthalene.

11. A process according to claim 1, wherein the solvent is benzonitrile.

12. A process according to claim 1, wherein the solvent is benzaldehyde or salicylaldehyde.

13. A process according to claim 1 or 2, wherein the solvent has a boiling point of 180° C. to 400° C.

14. A process according to claim 1, wherein the solvent separated by distillation from the reaction mixture after completion of the reaction is reused as a reaction medium.

15. A process according to claim 1, wherein the weight ratio of the amount of the solvent to the total amount of butadiene-1,3 and cyclopentadiene is 0.5 to 20.

16. A process according to claim 1, wherein the molar ratio of butadiene-1,3 to cyclopentadiene is from 0.5 to 3.0.

17. A process according to claim 16, wherein the reaction temperature is 120° to 250° C.

18. A process according to claim 17, wherein the reaction is carried out under a pressure necessary to allow the reaction to proceed in a liquid phase.

19. A process according to claim 18, wherein the reaction time is 15 minutes to 6 hours.

* * * * *